United States Patent [19]

Irwin

[11] Patent Number: 5,039,303
[45] Date of Patent: Aug. 13, 1991

[54] ORTHODONTIC PROCESS

[76] Inventor: Jere Irwin, 4604 Fechter Rd., Yakima, Wash. 98908

[21] Appl. No.: 585,812

[22] Filed: Sep. 20, 1990

[51] Int. Cl.$^5$ ................................................ A61C 3/00
[52] U.S. Cl. ........................................ 433/24; 433/215
[58] Field of Search .................................. 433/24, 215

[56] References Cited

U.S. PATENT DOCUMENTS 2,755,552  7/1956  Brandau ............................ 433/218
4,504,229  3/1985  Garito et al. ...................... 433/215

Primary Examiner—Gene Mancene
Assistant Examiner—Adriene B. Lepiane
Attorney, Agent, or Firm—Wells, St. John & Roberts

[57] ABSTRACT

A two-step orthodontic process is described in which a first weave 35 and a subsequent second weave 40 of fine dental floss are applied to a selected group of tooth crowns to effect correction of maloccluded teeth in the group. In the first weave a strand 10 of dental floss is placed in a figure "8" pattern about crowns 16 in the group. The strand 10 of material is secured in a knotless configuration by wedging the material of the strand 10 against the contact points 30 between adjacent teeth. The figure "8" pattern serves to span lingual 25 and facial surfaces 24 of the crowns in the group and to exert corrective forces against the teeth, causing them to move into prescribed desired alignment. In the second weave 40, a strand is applied with at least one span 41 of the strand across facial surfaces of the crowns 16 within the group. The span 41 is used to exert forces tending to gather and contour the crowns in a finishing technique. The initial, first weave 35 including a figure "8" pattern may be established to initially separate and begin positioning of the teeth. The second weave 40 is used to finish the procedure. A maloccluded crown 19 that requires torsion for correction may be corrected by winding the strand about the crown and pulling in one direction or another to produce a corrective torsional force.

19 Claims, 5 Drawing Sheets

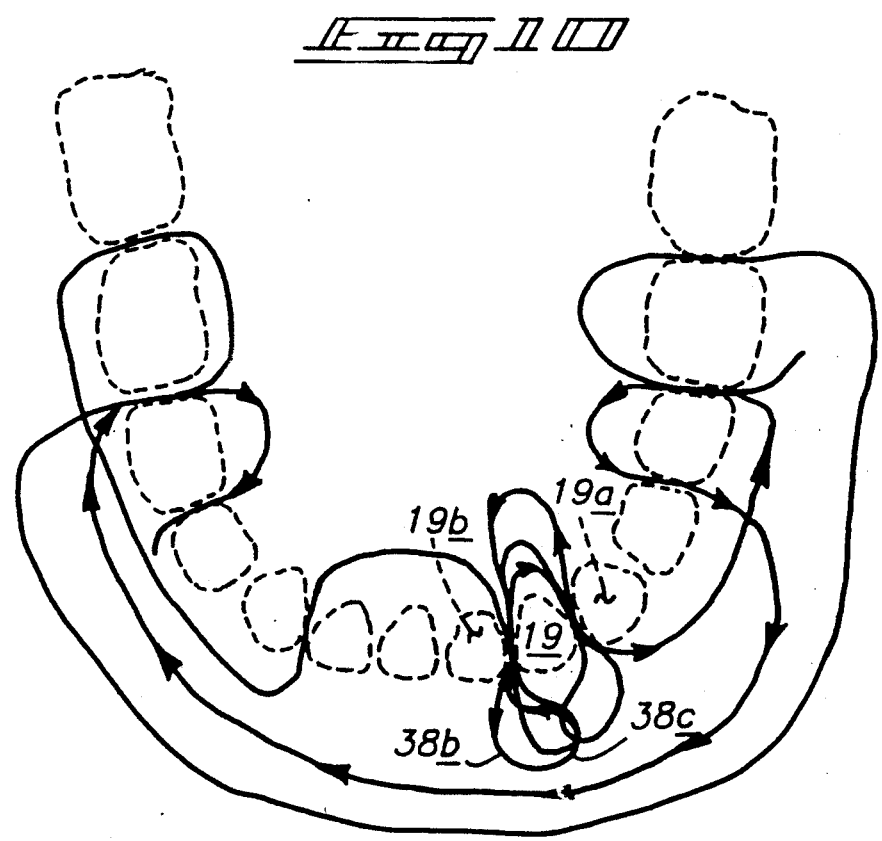

ORTHODONTIC PROCESS

TECHNICAL FIELD

The present invention relates to the field of orthodontics and more particularly to the process of correcting maloccluded crowns using a strand of thin material such as dental floss interwoven in a group of teeth.

BACKGROUND OF THE INVENTION

In the field of orthodontics, extremely complex and expensive procedures and apparatus are used for correcting "malocclusions" or crooked teeth. A "malocclusion" is simply a misaligned tooth or teeth in relation to the remaining teeth in a preferred arch configuration for the particular upper (maxillary) or lower (mandibular) arch. Often, one or more teeth protrude further lingually (inward) or facially (outward) than the remaining teeth in the arch. Another form of malocclusion includes excessive separation or proximation of adjacent teeth in an arch. Other forms of malocclusion include improper "torque" or rotation of a tooth about its long axis in relation to the desired arch configuration. These are relatively common forms of malocclusions and which are relatively usually correctable by applying corrective forces to the crowns with resulting movement of the crowns in a desired direction.

It is desirable to use an orthodontic procedure that may be self performed and that will thereby significantly reduce the expense of correcting malocclusion difficulties.

An attempt at a solution is described in the 1963 patent to Goldstein (U.S. Pat. No. 3,091,856). The Goldstein patent discloses an elastic thread ligature to be wrapped around crowns to correct malocclusion. The elastic thread is used in conjunction with a number of selectively placed knotted loops for holding the ligature in place. Opposed ends of the ligature are tied to anchor teeth to further secure the ligature in position.

The required elastic nature of this invention necessitates a relatively large cross sectional diameter for the ligature. The large cross sectional size of the ligature and loops limits the ability of the installer to correctly apply the ligature. Another shortcoming from the cross sectional diameter of the ligature and the loops is that, once in place, the ligature and loops have a tendency to separate the teeth, spreading the normal points of contact between adjacent teeth.

It is desirable to maintain point contact between adjacent teeth for a number of reasons. Firstly, the natural dental arch includes substantially all teeth in the arch with point contact between adjacent teeth. This serves to substantially unify the arch with all teeth assisting in support of one another. The point contact between adjacent teeth also protects the underlying interproximal gingival tissue from trauma during chewing. The point contact between adjacent teeth also serves to keep food from being received and trapped between the adjacent teeth and against the interproximal gingival tissue. Such undesirable separation of the crowns may occur due to use of large diameter ligature.

Another problem found with the Goldstein type ligature is the need to use knots to hold the ligature at prescribed tension, and to form the auxiliary loops between adjacent crowns. Knots are difficult to tie in the patient's mouth and thus limit the ability of the patient to self-administer the ligature.

There thus remains a need for an inexpensive, simple, yet effective orthodontic process by which simple malocclusions, especially along the anterior or front teeth may be corrected by a self administration of the corrective process.

It is therefore a primary object of the present invention to provide an orthodontic process for correcting malocclusions in which individuals may perform the process themselves.

A further object is to provide such a process in which the correction of malocclusions may be accomplished using simple materials such as ordinary thin dental floss.

A still further object is to provide such a process in which the applied corrective materials such as dental floss is inconspicuous when in place on the selected crowns.

A yet further object is to provide such a process that will quickly and effectively correct simple malocclusions.

These and still further objects and advantages will become apparent from the following detailed description which, along with the accompanying drawings, disclose a preferred form of the present invention.

BRIEF DESCRIPTION OF THE DRAWINGS

A preferred process is described using steps exemplified in the drawings in which:

FIG. 10 is a diagrammatic view of an alternate wrap used for applying torque to a specific maloccluded tooth.

DETAILED DESCRIPTION OF THE PREFERRED EMBODIMENTS

The following disclosure of the invention is submitted in furtherance with the constitutional purpose of the Patent Laws "to promote the progress of science and useful arts" (Article 1, Section 8).

The process of the present invention generally makes use of an elongated strand 10 of fine strong material such as dental floss. The selected strand 10, in the preferred process, is selected from various grades of commercially available dental floss of the "fine" or "extra fine" floss material. Such floss is typically a stretched nylon fiber material and is sold in a number of configurations and textures. The preferred floss is produced by Johnson and Johnson and is labeled as "fine" or "extra fine" unwaxed dental floss. This form of floss is preferred due to its relative strength and the ease in which such fine material may be placed between adjacent teeth.

The selected strand 10 extends a distance of approximately 18 to 24 inches between free ends 12. The length of floss is inserted or woven in a prescribed manner about individual crowns within the selected dental arch to apply corrective forces to the engaged crowns of that arch.

Before describing the process for applying the strand 10, a brief description will be given of general anatomical features that will aid in understanding the present process.

The teeth shown are arranged in a dental arch 13. The arch 13 shown is the mandibular or lower arch. However, the upper or maxillary arch may be utilized with the present method as well. In fact, it may be desirable to perform the present process on the upper and lower arches simultaneously.

Figure 7:
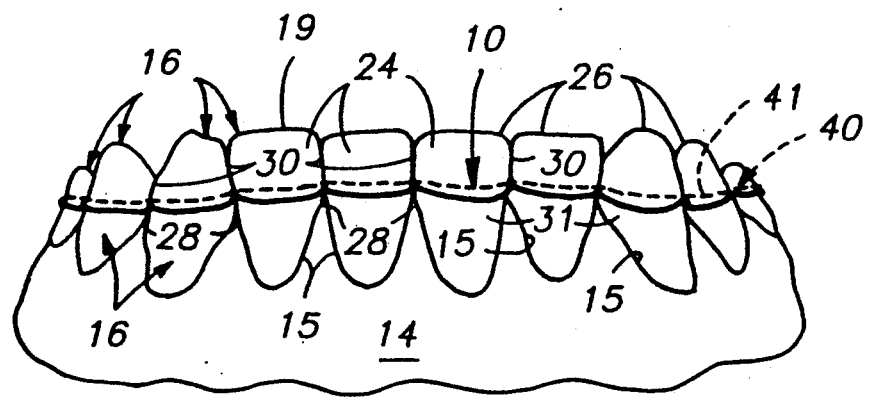
FIG. 7 is a front elevational view illustrating placement of the strand in relation to the occlusal plane of the associated crowns.

Crowns 16 within the arch project axially outward from the gingiva or gums 14 (FIG. 7). The junction of the crowns 16 and gingiva 14 is termed the gingival margin 15. Certain of the crowns 16 in the arch may be maloccluded. Such crowns are referred to as maloccluded crowns 19.

Each crown 16 includes an outwardly facing facial surface 24. Each crown 16 also includes an inwardly facing lingual surface 25. The crowns 16 extend along central tooth axes (not shown) from the gingival margin 15 to relatively horizontal chewing surfaces 26. The chewing surfaces 26 together are formed along a slightly curved "occlusal plane".

Interstices 28 (FIG. 7) are formed between adjacent crowns 16. The interstices 28 are typically triangular openings formed between adjacent teeth. Interstices 28 are located axially along the teeth axes between the gingival margins 15 or interproximal gingival tissue, and the contact points 30.

Middle portions 31 of the crowns are defined as those parts of the crowns bordering the interstices 28, between the contact points 30 and the gingival margin 15. More specifically, and for purposes of this description, the middle portions of the crown surfaces are situated just slightly toward the gingival margin 15 from the contact points 30.

Figure 3:
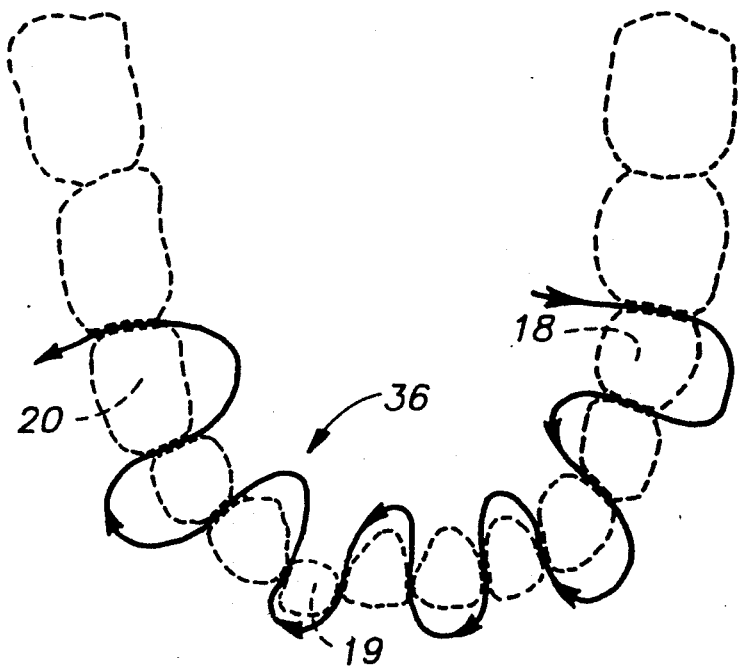
FIG. 3 is a view of the arch of FIG. 1 with a first course of strand being applied, the crowns of the arch being shown by dashed lines and the strand by a diagrammatic wide solid line.

A group of crowns 16 is selected for treatment using the present process. The selected group preferably includes 10 successive crowns 16 extending about the arch from a first anchor crown 18 (FIGS. 3-5) and inclusive of one or more maloccluded crowns 19 and ending at a second anchor crown 20. It is pointed out that the group of selected crowns 16 is determined by the nature of the malocclusion and that more or fewer crowns 16 may be included in the selected group. However, it is preferred that the group include strong premolar or molar crowns for the first and second anchor crowns 18, 20.

The present process, in general terms, involves the steps of inserting the elongated strand 10 of fine dental floss into the interstices 28 between adjacent crowns 16 of a selected group of teeth. In initial stages of the process, the strand 10 is formed in a progressive FIG. "8" pattern in a first weave 35 about successive crowns in the selected group. The loops of the figure "8" pattern are placed to receive the facial and lingual surfaces of the successive crowns. The strand is pulled taut across the maloccluded crown or crowns 19 within the group and the free ends 12 of the strand are secured in a knotless condition against at least one of the selected anchor crowns. Securement of the free strand ends 12 may be accomplished simply by wedging the strand 10 against the contact points between one of the anchor crowns 18 or 20 and an adjacent crown 16.

The process involves two stages, first, using the first weave 35 (FIGS. 3, 4, 8) subsequently a second weave 40 (FIGS. 5, 9) respectively. Both weaves 35, 40 are formed by a strand 10 of fine dental floss between the crowns 16.

Figure 4:
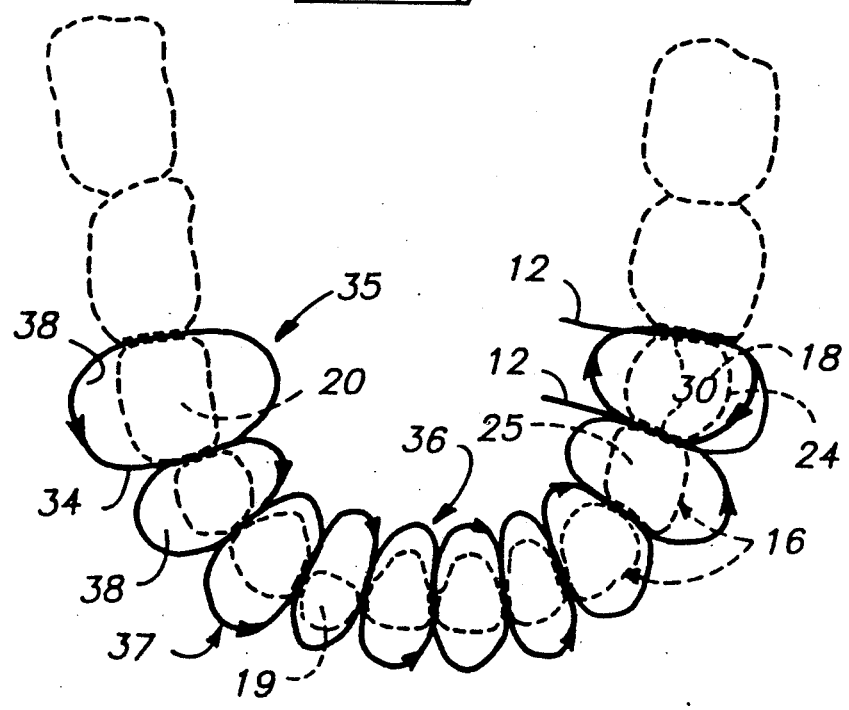
FIG. 4 is a view similar to FIG. 3 only showing a second course of the strand applied to the crowns in the arch, thereby completing a first weave.

The first weave 35 is started in a first course 36 (FIG. 3) and ends in a second course 37 (FIG. 4). The first course 36 extends in a first direction from a first anchor crown 18 toward the second anchor crown 20. The strand 10 is interlaced in a sinuous passage between successive crowns 16 such that the facial surface 24 of one crown 16 is spanned by the strand 10, and the lingual surface 25 of the next successive crown 16 is spanned by the strand 10, and so on.

The strand 10 is interlaced between the facial and lingual surfaces 24, 25 of the crowns 16, making the transition between the surfaces 24, 25 through the interstices 28 between adjacent crowns 16 in the group until the second anchor crown 20 is reached.

After the second anchor crown is reached, the direction is reversed and the remaining uncovered facial and lingual surfaces 24, 25 of the crowns are covered by the second course 37 of the first weave 35. The second course 37 is essentially a repetition of the first course 36 in the opposite direction and about opposite surfaces of the successive crowns.

As the above steps are accomplished, tension is placed along the length of the strand in both courses 36 and 37 to introduce corrective forces to the maloccluded teeth in the group.

The drawings, with the exception of FIG. 7 show the courses 36 and 37 loose. This is done simply to illustrate the direction and nature of the weave. In actual practice the strand will be pulled taut as it is placed along the courses 36, 37. Care is also taken at this point to maintain the strand along a plane adjacent to the middle surfaces 31. Thus, the woven strand 10 will maintain a configuration substantially parallel to the occlusal plane of the associated crowns as shown in FIG. 7.

Placement of the strand adjacent to the points of contact 30 assures that the gingiva will not be irritated by the strand material, and that maximum corrective forces may be applied through the crowns 16 to their associated roots (not shown).

It is pointed out that the starting point for applying the strand 10 may occur between any successive teeth or crowns 16 within the selected group. However, it is preferred that the starting point be at one of the anchor crowns 18 or 20 and that the start be initiated with a free end 12 of the strand 10 situated along the lingual surfaces 25 of the crowns 16. This places the free end 12 of the strand 10 within the mouth cavity in an inconspicuous location. In this manner, the free end 12 may have sufficient length to enable gripping between the thumb and index finger for removal purposes at a later time.

On completion of the second course 37, it is preferred that both free ends 12 of the strand be situated within the mouth cavity in a similar location. The second course 37 may be secured by one or more wraps about the first anchor crown 18 and by wedging the wraps against an associated contact point 30 to assure that the tension placed along the length of the strand 10 will be maintained during the time the strand is in place on the group of crowns 16.

The final figure "8" pattern of the first weave 35 shown in FIG. 4, is formed of a progression of loops 38 formed by the first and second courses 36, 37. Each of the loops 38 receives a crown 16. The loops 38 cross within the interstices 28 and if urged against the points of contact 30, will serve to slightly separate the crowns 16 within the group over a period of time.

Figure 8:
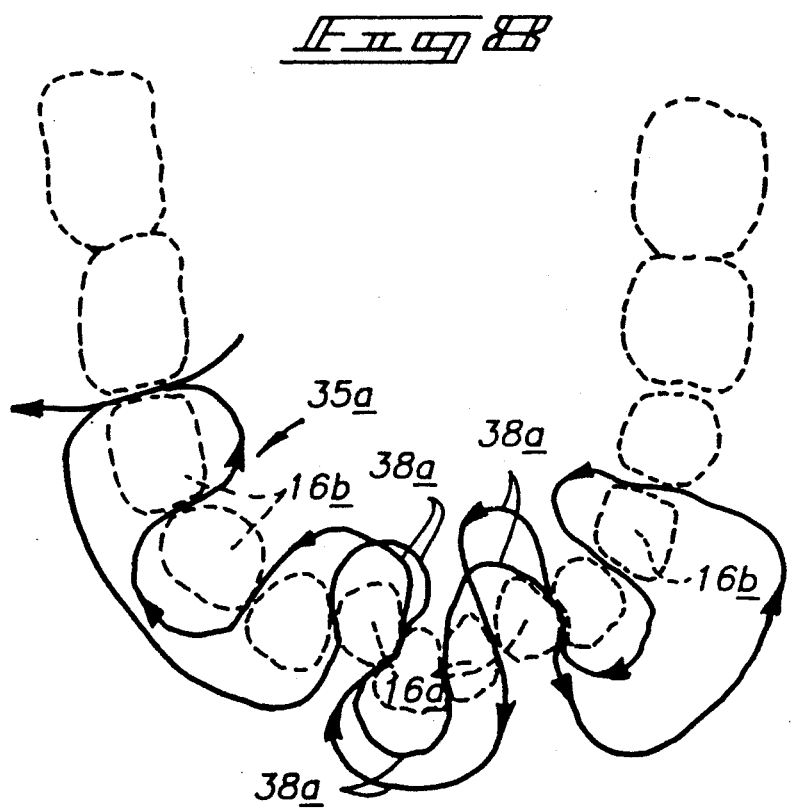
FIG. 8 is a diagrammatic view showing an alternate form of the first weave.

An alternative form of the first wrap is shown at 35a in FIG. 8. In this configuration selected loops 38a are doubled over selected crowns 16a, while other teeth 16b are simply engaged by single strand segments. This configuration may be used to selectively increase the corrective forces on a specific maloccluded tooth or small selected groups of maloccluded teeth 16a.

Figure 6:
FIG. 6 is a diagrammatic view illustrating a step for torque correction of a single maloccluded tooth.

FIGS. 6 and 10 show a process by which a desired "torque" may be applied during application of either weave 35 or 40 to a tooth that is rotated out of a desired alignment with the remainder of the arch. The strand 10 is simply wrapped around the selected maloccluded crown 19 in a direction that will result in the application of torsion on the engaged crown 19 when the strand 10 is pulled taut on one side of the winding. The taut strand 10 and directional wrap will have the tendency to rotate the engaged maloccluded crown 19 in the direction of pull as indicated by the arrow in FIG. 6. Thus, if tension is greater on one side of the strand 10, the engaged maloccluded crown 19 will be subjected to torsion in that direction. The corrective forces are determined by the rotated position of the maloccluded crown 19 and the direction of rotation required to move it back into the proper arch form with the remaining crowns 16 in the group.

Figure 5:
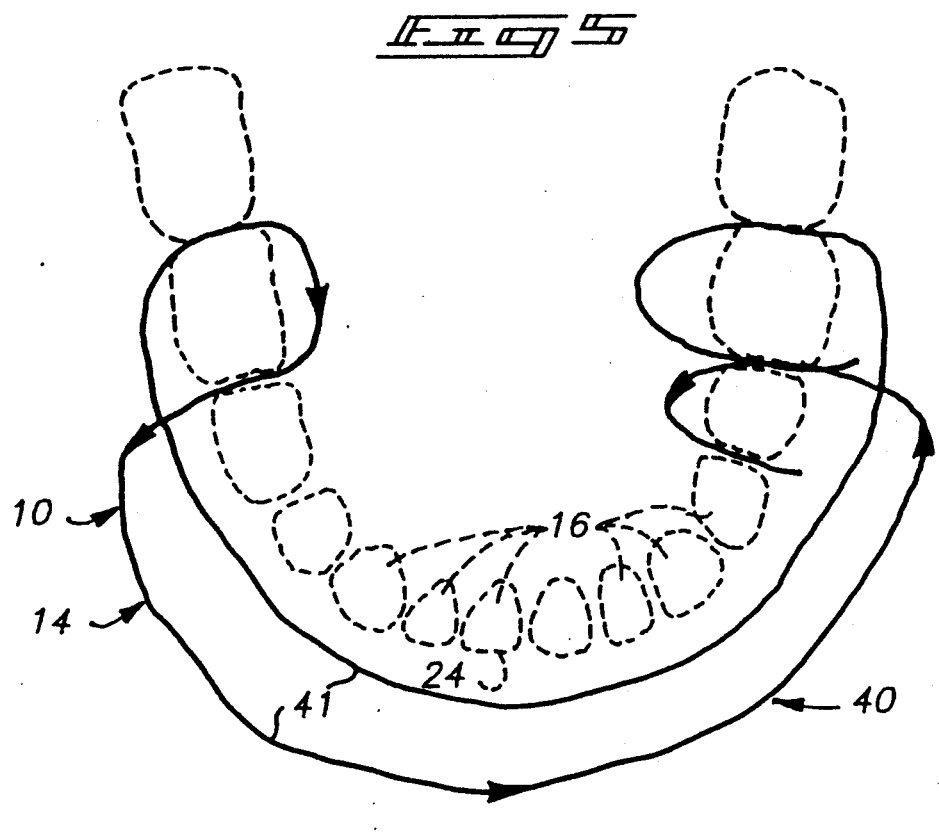
FIG. 5 is a view illustrating a second weave.

A variation of the "torque" application technique is shown in FIG. 10 in conjunction with an exemplary contouring wrap that is described below and more particularly in relation to FIGS. 5 and 9. In FIG. 10, a maloccluded crown 19 is first captured by a loop of the floss. The floss length is doubled on itself, forming a bight or loop 38b that is inserted first between the tooth 19 and an adjacent tooth 19a, then between tooth 19 and an opposite adjacent tooth 19b. The closed end 38c of the bight then projects to the labial or facial side of the tooth. The free ends of the floss are then passed though the exposed bight end 38c, forming a slip "hitch" to secure the loop to the tooth 19. The free ends of the floss may then be wound about the tooth as shown in FIG. 10 and as described above in conjunction with FIG. 6 to apply a desired torque to the tooth when the floss ends are pulled taut. The remaining lengths of floss may then be woven between adjacent teeth of the selected group, as shown in FIG. 10, to apply corrective forces thereto and to maintain torsional tension on the windings around the tooth 19. The floss may also be woven between adjacent teeth in other patterns suggested herein or modifications thereof.

It is preferred that the selected first weave 35 or 35a and steps described to this point be applied on a daily basis for a period of several weeks to initiate preliminary corrective movement of the crowns 16.

Following the preliminary alignment established using the initial first weave 35, a second weave 40 is added to contour the previously positioned teeth in a proper arch configuration. Initially, second weave 40 may be applied at night following removal of the first weave 35 which is used during the day time. Later, the first weave is discontinued and only the second weave is applied.

Ends of the second weave 40 (FIG. 5) are secured in the same manner as the first weave 35. At least one span 41 of the strand 10 is secured across selected multiple successive facial surfaces 24 of the crowns 16 in the group. The span 41 is pulled taut against the surfaces 24 to organize the selected crowns in the group into proper alignment and to move them together once again to bring the contact points 30 (FIG. 7) into proper relationships.

The span 41 extends across the middle portions 31 (see dashed line 41 in FIG. 7) of the crowns 16 and may overlap the points of contact 30 between the adjacent crowns of the group. The first weave 35 or 35a of the strand 10 forming the figure "8" pattern, on the other hand, is situated just below the contact points 30, as shown in FIG. 7. The strand 10 from the second weave 40 is preferably applied daily until final alignment of the crowns in the group into corrected positions in the arch occurs. The amount of time taken to accomplish this is determined by the nature of the corrections taking place and the amount of force applied by the strand 10 that feels comfortable to the user.

Figure 9:
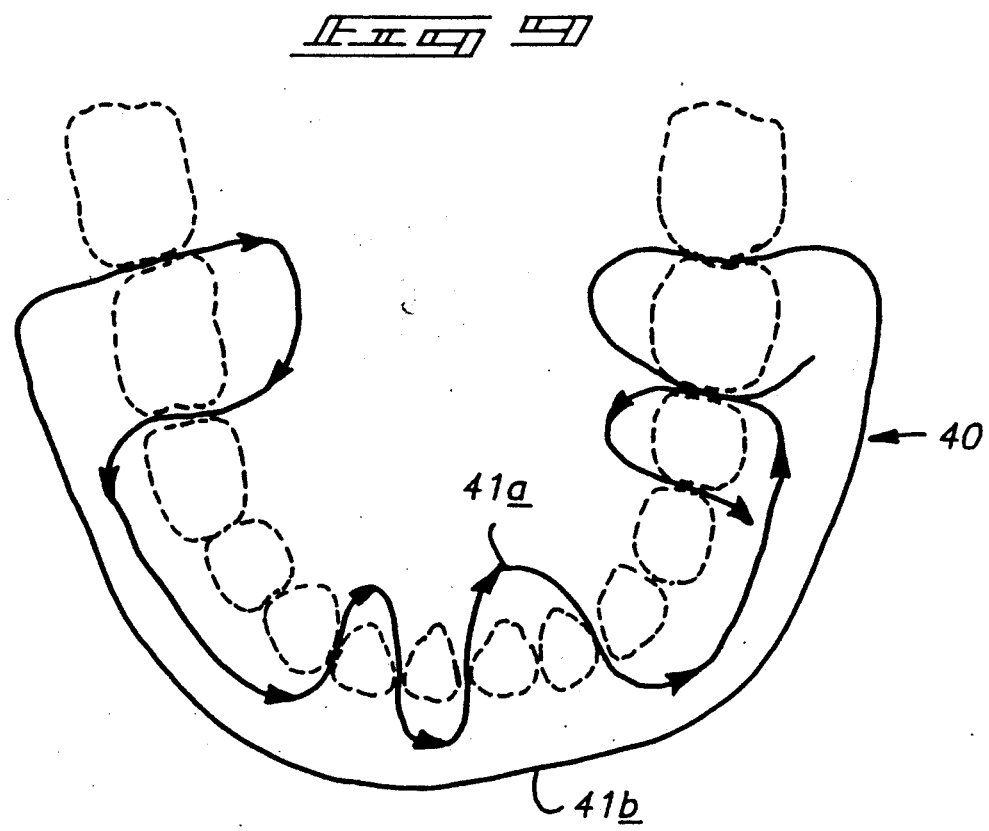
FIG. 9 is a diagrammatic view showing an alternate form of a second weave.

A variation of the second weave is shown in FIG. 9 wherein a weave 41a is shown in addition to a single strand contouring wrap 41b across the crown facial surfaces. The weave 41a produces added force to any selected teeth that may have a tendency during the correction period to migrate back to their original maloccluded positions. Note, a single strand of the floss length is used without the figure "8" pattern crossing between adjacent teeth to avoid the spacing effect that is no longer desired at this point. To further avoid unwanted spacing between adjacent teeth, the weave 41a should be carefully situated axially within the interstices along the teeth, between their contact points and the adjacent gingival margins.

Figure 1:
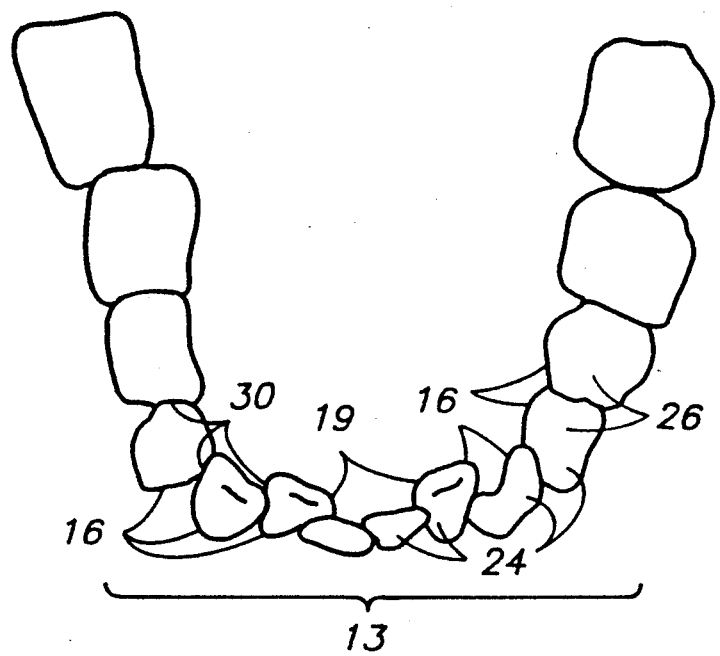
FIG. 1 is a view of a dental arch with malocclusions before treatment using the present process.
Figure 2:
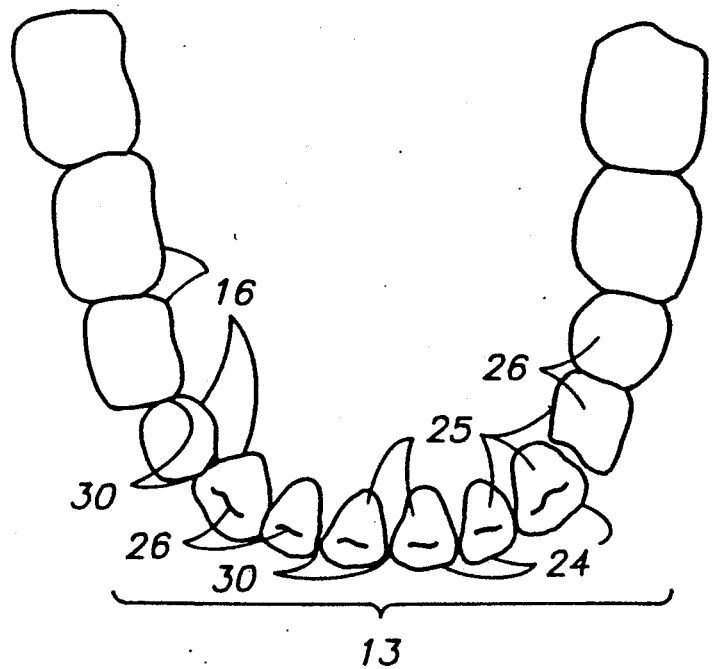
FIG. 2 is a view of the same dental arch following application of the present orthodontic process.

The correction illustrated between FIGS. 1 and 2 was accomplished by the Applicant over a period of approximately six months. It is pointed out that in the arch shown (which was diagrammed from models of the Applicant's mandibular arch) was initially the subject of professional orthodontic procedures in which an appliance was provided by an Orthodontist to precede the present treatment by spreading the rear molars. The process for correcting the maloccluded crowns was then completed only by use of the present process.

Dental floss is considerably elastic when stretched. When it is tightly wrapped in a continued figure "8" pattern around crowns 16, it will separate and apply the most corrective pressure to the teeth the furthest out of alignment. The figure "8" pattern may be repeated, or extra loops may be added as suggested above with reference to FIG. 8, to apply additional correctional forces. Each additional course applies more pressure.

The user determines by "feel" how much force to apply the strands. If the wrap hurts too much, especially when the process is being first started, the user may simply remove the strand and try the process again, using less tension and fewer wraps.

Each course is preferably finished with the strand ends 12 between two tightly spaced crowns 16. The strand ends 12 may be carefully cut off close to the crowns 16 and, preferably, within the mouth cavity.

It is pointed out that the entire process described herein is accomplished without the need to tie knots in the strand 10. Nor is there any need to provide any materials in addition to the strand 10. No loops or dividers are used, nor are there any anchoring devices required to secure the strand ends 12 to the crowns 16. The entire process is therefore easily carried out by the individual, without need for assistance. The strand 10 maybe secured wherever necessary simply by wrapping or by wedging it between adjacent crowns and the associated point of contact 30.

The initial figure "8" wrap of the first weave 35 may be left on for two or three days without changes. However, daily changing is recommended. To remove the strand 10, the user may simply pull the free ends 12 from engagement with the engaged crowns 16, or cut the strand 10 with a small sharp knife if necessary. Care must be taken, however, not to scratch the enamel or to cut the gingival tissues. The user may then pull the ends of the strand with tweezers or needle-nosed pliers.

It is pointed out that there are many possibly wrapping configurations conceivable using the present process. The procedure using the first weave 35 with the figure "8" pattern, followed by the second weave 40 and its addition of the span 41 functions preferably in most situations.

The first weave 35 with the figure "8" pattern is very inconspicuous and can be easily used during the day. This application results in the spreading and straightening of the crowns 16 involved by applying pressure to the maloccluded crowns 19 furthest out of alignment.

The second weave 40, including the span 41 is to be used after the initial spacing and repositioning is achieved using the first weave 35 or variations thereof. The second weave serves to gather and contour the teeth within the arch, lending the finishing touch to the treatment.

The present treatment can provide excellent results in seemingly impossible cases, even on older people. It is additionally beneficial because it cleans the teeth and is especially healthy for the gums. In experimental use, there have been no ill effects shown, even with extra tension applied to the strand in the first and second weaves 35, 40. In fact, additional figure "8" courses and spans 41 have been applied to provide even greater corrective and aligning forces to accomplish results in relatively shorter periods of time. The determinative factor appears to be the conspicuousness of the strands and the amount of time to which the user wishes to devote to the wrapping procedures.

In compliance with the statute, the invention has been described in more or less specific language. It is to be understood, however, that the invention is not limited to the specific steps and features shown, since the means and process steps herein disclosed comprise a preferred form of putting the invention into effect. The invention is, therefore, claimed in any of its forms or modifications within the proper scope of the appended claims appropriately interpreted in accordance with the doctrine of equivalents.

I claim:

1. In an orthodontic process, the steps of:
   inserting an elongated strand of dental floss into interstices between crowns of a selected group of teeth including at least one maloccluded crown and selected anchor crowns at opposed ends of the selected group;
   forming the strand in a progressive figure "8" pattern about crowns in the selected group with the figure "8" pattern receiving facial and lingual surfaces of the crowns and;
   pulling the strand taut; and
   securing free ends of the strand in a knotless condition against at least one of the selected anchor crowns.

2. The orthodontic process of claim 1 including the step of orienting the figure "8" pattern along longitudinal middle sections of the crowns between contact points of the crowns of the selected group and the adjacent gingival margin.

3. The orthodontic process of claim 1 including the step of placing the free ends of the strand to the lingual side of the selected group of teeth.

4. The orthodontic process of claim 1 including the step of wrapping the strand about a selected maloccluded crown in a prescribed direction and pulling the strand taut on one side of the wrapping to produce a corrective torque on the maloccluded crown.

5. The orthodontic process of claim 1 including the step of aligning the figure "8" pattern substantially parallel to the occlusal plane of the selected group of teeth.

6. The orthodontic process of claim 1 including the subsequent step of wrapping a span of the strand across selected multiple successive facial surfaces of the crowns in the selected group of teeth.

7. The orthodontic process of claim 1 including the subsequent step of wrapping a span of the strand across selected multiple successive facial surfaces of the crowns in the group; and wrapping the strand about a selected maloccluded crown in a prescribed direction and pulling the strand taut on one side of the wrapping to produce a corrective torque on the maloccluded crown.

8. In an orthodontic process, the steps of:
   selecting a group of crowns within an arch in which at least one maloccluded crown is situated between anchor crowns at opposed ends of the group;
   interlacing a strand of thread through interstices between successive crowns of the group in a progressive, knotless figure "8" pattern taut against the facial and lingual surfaces of crowns in the group to exert corrective separation and alignment forces against the malocclusion; and
   securing the strand between adjacent crowns having contact points by wedging the strand against the contact points to secure and hold the strand taut.

9. The orthodontic process of claim 8 including the subsequent step of wrapping a span of the strand across selected multiple successive facial surfaces of the crowns in the group.

10. The orthodontic process of claim 8 including the step of aligning the figure "8" pattern substantially parallel to the occlusal plane of the crowns in the arch in which the group of crowns are situated.

11. The orthodontic process of claim 8 including the subsequent step of wrapping a span of the strand across selected multiple successive facial surfaces of the crowns in the group; and
   aligning the span of strand substantially parallel to the occlusal plane of the crowns in the arch in which the group of crowns are situated.

12. The orthodontic process of claim 8 including the step of wrapping the strand about a selected maloccluded crown in a prescribed direction and pulling the strand taut on one side of the wrapping to produce a corrective torque on the maloccluded crown.

13. The orthodontic process of claim 8 including the step of aligning the figure "8" pattern substantially parallel to the occlusal plane of the group of crowns; and wrapping the strand about a selected maloccluded crown in a prescribed direction and pulling the strand taut on one side of the wrapping to produce a corrective torque on the maloccluded crown.

14. The orthodontic process of claim 8 including the subsequent step of:
   wrapping the strand about a selected maloccluded crown in a prescribed direction and pulling the strand taut on one side of the wrapping to produce a corrective torque on the maloccluded crown; and
   wrapping ends of the strand across selected multiple successive facial surfaces of the crowns in the group.

15. The orthodontic process of claim 8 including the step of placing the free ends of the strand to the lingual side of the crowns.

16. An orthodontic process for straightening maloccluded tooth crowns in an arch, comprising the steps of:
   selecting a group of crowns within the arch in which at least one maloccluded crown is situated between selected anchor crowns at opposed ends of the group;
   progressively forming a first weave with a strand of fine dental floss between the crowns of the group in a first course in which the weave extends in a first direction from a first anchor crown of the group by first spanning a facial surface or a lingual surface of a crown of the group adjacent the first anchor crown, then spanning the opposed facial surface or a lingual surface of the next successive crown in the group, and by repeating the weave to the second anchor crown, then reversing the first direction at the second anchor crown and continuing the weave in the opposite direction back to the first anchor crown, thereby forming a figure "8" pattern about selected crowns in the group with loops of the figure "8" encircling the selected crowns of the group; and
   pulling the strand taut across the crowns of the group to apply corrective forces to the crowns;
   leaving the first weave in place on the group of crowns for a selected period of time to effect separation and partial alignment of the crowns in the group;
   removing the first weave;
   progressively forming a second weave with a strand of dental floss by
      (a) anchoring one end between adjacent crowns,
      (b) applying at least a span of the strand across selected multiple successive facial surfaces of the crowns in the group, (c) pulling the span taut, and (d) anchoring the remaining end of strand between adjacent crowns;
   leaving the second weave in place on the group of crowns for a selected period of time to effect final alignment of the crowns in the group; and
   removing the second weave following final alignment of the crowns in the group.

17. An orthodontic process for aligning and contouring crowns within a selected group in an arch, comprising the steps of:
   progressively forming a weave with a strand of dental floss by (a) anchoring one end of the dental floss between two adjacent teeth at one end of the group, (b) pulling a span of the floss across selected multiple successive facial surfaces of the crowns in the group, and (c) anchoring the remaining end of the floss in a knotless condition between adjacent crowns of the group;
   leaving the weave in place on the group of crowns for a selected period of time to effect alignment of the teeth in the group; and
   removing the weave following alignment of the teeth in the group.

18. The orthodontic process of claim 17 in further comprising the step of substantially aligning the span of floss with contact points of the teeth in the group.

19. The orthodontic process of claim 17 including the further step of weaving a portion of the strand independently of the span pulled across the facial surfaces, between selected teeth in the group.

* * * * *